(12) United States Patent
Collins et al.

(10) Patent No.: US 8,058,393 B2
(45) Date of Patent: *Nov. 15, 2011

(54) MICROWAVE-ASSISTED PEPTIDE SYNTHESIS

(75) Inventors: Jonathan McKinnon Collins, Charlotte, NC (US); Joseph Joshua Lambert, Charlotte, NC (US); Michael John Collins, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/549,445

(22) Filed: Aug. 28, 2009

(65) Prior Publication Data

US 2010/0048865 A1 Feb. 25, 2010

Related U.S. Application Data

(63) Continuation of application No. 12/143,979, filed on Jun. 23, 2008, now Pat. No. 7,582,728, which is a continuation of application No. 10/604,022, filed on Jun. 23, 2003, now Pat. No. 7,393,920.

(51) Int. Cl.
*C07K 1/00* (2006.01)
*C07K 5/00* (2006.01)
*C07K 7/00* (2006.01)
*C07K 16/00* (2006.01)
*C07K 17/00* (2006.01)
*A61K 38/00* (2006.01)

(52) U.S. Cl. ......... 530/333; 530/335; 530/336; 530/337

(58) Field of Classification Search .................. None
See application file for complete search history.

(56) References Cited

U.S. PATENT DOCUMENTS

| | | |
|---|---|---|
| 3,531,258 A | 9/1970 | Merrifield et al. |
| 3,581,190 A | 5/1971 | Brown |
| 3,647,390 A | 3/1972 | Kubodera et al. |
| 3,926,556 A | 12/1975 | Boucher |
| 4,192,798 A | 3/1980 | Fuller et al. |
| 4,696,981 A | 9/1987 | Harada et al. |
| 4,746,490 A | 5/1988 | Saneii |
| 5,288,464 A | 2/1994 | Nokihara |
| 5,380,495 A | 1/1995 | Chang et al. |
| 5,382,414 A | 1/1995 | Lautenschlager |
| 5,387,397 A | 2/1995 | Strauss et al. |
| 5,830,417 A | 11/1998 | Kingston |
| 5,932,075 A | 8/1999 | Strauss et al. |
| 6,028,172 A | 2/2000 | Stepaniuk et al. |
| 6,034,361 A | 3/2000 | Hudak |
| 6,171,555 B1 | 1/2001 | Cargill et al. |
| 6,288,379 B1 | 9/2001 | Greene et al. |
| 6,320,025 B1 | 11/2001 | Slavazza et al. |
| 6,326,090 B1 | 12/2001 | Schultz et al. |
| 6,486,455 B1 | 11/2002 | Merabet |
| 6,630,652 B2 | 10/2003 | Jennings |
| 6,713,719 B1 | 3/2004 | De Steur et al. |
| 6,744,024 B1 | 6/2004 | Hayes et al. |
| 6,858,434 B1 | 2/2005 | Williams |
| 6,867,400 B2 | 3/2005 | Collins et al. |
| 6,917,023 B2 | 7/2005 | Hayes et al. |
| 7,393,920 B2 | 7/2008 | Collins et al. |
| 2002/0117498 A1 | 8/2002 | Jennings |
| 2003/0082633 A1 | 5/2003 | Martin et al. |
| 2003/0089706 A1 | 5/2003 | Jennings |
| 2003/0199099 A1 | 10/2003 | King et al. |
| 2004/0020923 A1 | 2/2004 | Collins et al. |
| 2006/0025567 A1 | 2/2006 | Collins et al. |
| 2006/0025568 A1 | 2/2006 | Collins et al. |
| 2006/0025569 A1 | 2/2006 | Collins et al. |
| 2007/0090104 A1 | 4/2007 | Collins et al. |
| 2007/0270573 A1 | 11/2007 | Collins |
| 2009/0012264 A1 | 1/2009 | Collins et al. |
| 2009/0221792 A1* | 9/2009 | Collins et al. .................. 530/334 |
| 2010/0048865 A1* | 2/2010 | Collins et al. .................. 530/334 |

FOREIGN PATENT DOCUMENTS

| | | |
|---|---|---|
| EP | 0 541 340 A2 | 5/1993 |
| EP | 1 491 552 A2 | 12/2004 |
| EP | 1 533 025 A2 | 5/2005 |
| WO | 2004/002617 A1 | 1/2004 |

OTHER PUBLICATIONS

European Search Report of foreign counterpart application No. EP05101287.0; mailed Nov. 21, 2007; 3 pages.
Ferguson, "Focused microwave instrumentation from CEM Corporation," Molecular Diversity 2003, vol. 7, Nr. 2-4, pp. 281-286.
Park, et al., "New Reaction Vessel for Solid-Phase Peptide Synthesis," Canadian Journal of Biochemistry, National Research Council of Canada, Ottawa, vol. 50, No. 7, Jan. 1972, pp. 755-757.
Caddick, "Microwave Assisted Organic Reactions," Tetrahedron 1985, United Kingdom, vol. 51, No. 38, 1995; pp. 10403-10432.
Kramer et al, "Synthesis and Screening of Peptide Libraries on Continuous Cellulose Membrane Supports", Methods in Molecular Biology, vol. 87: Combinatorial Peptide Library Protocols; Humana Press, Inc.; Totowa, NJ; pp. 25-39, Dec. 1997.
Hilpert et al., "Anti-c-myc antibody 9E10: epitope key positions and variability characterized using peptide spot synthesis on cellulose," Protein Engineering, Oct. 2001, vol. 14, No. 10, pp. 803-806.
Frank, "The Spot-synthesis technique. Synthetic peptide arrays on membrane supports-principles and applications," 2002, Journal of Immunological Methods. vol. 267, pp. 13-26.
Overview of Peptide Synthesis. Anaspec. Accessed online Feb. 15, 2006 at http:/www.anaspec.com/html/peptide_notes. html, pp. 1-11.

(Continued)

*Primary Examiner* — Marcela M Cordero Garcia
(74) *Attorney, Agent, or Firm* — Summa, Additon & Ashe, P.A.

(57) ABSTRACT

An instrument and method for accelerating the solid phase synthesis of peptides are disclosed. The method includes the steps of deprotecting a protected first amino acid linked to a solid phase resin by admixing the protected linked acid with a deprotecting solution in a microwave transparent vessel while irradiating the admixed acid and solution with microwaves, activating a second amino acid, coupling the second amino acid to the first acid while irradiating the composition in the same vessel with microwaves, and cleaving the linked peptide from the solid phase resin by admixing the linked peptide with a cleaving composition in the same vessel while irradiating the composition with microwaves.

27 Claims, 8 Drawing Sheets

OTHER PUBLICATIONS

Kappe, "Speeding Up Solid-Phase Chemistry by Microwave Irradiation. A Tool for High-Throughout Synthesis," American Laboratory, 2001, vol. 33, No. 10, pp. 13-16 and 18-19.

Murray et al., "Efficient Synthesis of a B-Peptide Combinatorial Library with Microwave Irradiation," JACS. 2005, vol. 127, pp. 13271-13280.

Al-Obeidi et al., "Microwave-Assisted Solid-phase Synthesis (MASS): Parallel and Combinatorial Chemical Library Synthesis," Mini Reviews in Medicinal Chemistry. 2003, vol. 3, pp. 449-460.

Lew et al., "Increasing Rates of Reaction: Microwave-Assisted Organic Synthesis for Combinatorial Chemistry," J Comb Chem. Mar./Apr. 2002. vol. 4, No. 2, pp. 95-105.

Lange et al., "Recent Advances in Microwave-Assisted Combinatorial Synthesis and Library Generation," Combinational Chemistry and High Throughput Screening. 2005, vol. 8, pp. 595-606.

Scharn et al., "Spatially Addressed Synthesis of Amino-and Amino-Oxy-Substituted 1,3,5-Triazine Arrays on Polymeric Membranes," J Comb Chem. 2000, vol. 2, pp. 361-369.

Scharn et al., "Sequential Nucleophilic Substitution on Halogenated Triazines, Pyrimidines, and Purines: A Novel Approach to Cyclic Peptidomimetics," J Org Chem. 2001, vol. 66, pp. 507-513.

Wang et al., Enhancement of Coupling Reaction in Peptide Synthesis by Microwave Irradiation, 12 pages. 1990, 1992 and 1997.

Merrifield, "Concept and early development of solid-phase peptide synthesis," Methods Enzymol. 1997; 289: 3-13.

Albericio et al., "Coupling Reagents and Activation," Methods Enzymol. 1997; 289: 104-126.

Erdelyi et al., "Rapid Microwave-assisted Solid Phase Peptide Synthesis," Synthesis 2002 Germany, No. 11, 2002 Germany, No. 11, 2002, pp. 1592-1596.

Yu et al., "Enhanced Coupling Efficiency in Solid-Phase Peptide Synthesis by Microwave Irradiation," Journal of Organic Chemistry, vol. 57, No. 18, 1992, pp. 4781-4784.

Santagada, et al. "Microwave-Enhanced Solution Coupling of the Alpha, Alpha-dialkyl Amino Acid, Aib, "Tetrahedron Letters, vol. 42, No. 31, Jul. 30, 2001, pp. 5171-5173.

Daga, et al., "Rapid Microwave-Assisted Deprotection of N-Cbz and N-Bn Derivatives," Tetrahedron Letters, Jul. 30, 2001 United Kingdom, vol. 42, No. 31, pp. 5191-5194.

Collins, et al., "Novel Method for Enhanced Solid Phase Peptide Synthesis Using Microwave Energy," Biopolymers, vol. 71, No. 3, 2003, p. 361.

Porcheddu et al., "A New, Rapid, General Procedure for the Synthesis of Organic Molecules Supported on Methoxy-Polyethylene Glycol (MeOPEG) under Microwave Irradiation Conditions," Eur. J. Org. Chem. 2003, pp. 907-912.

Kramer et al., "Combinatorial Cellulose-Bound Peptide Libraries: Screening Tools for the Identification of Peptides that bind Ligands with Predefined Specificity," Methods: A companion to Methods in Enzymology. 1994, vol. 6, pp. 388-395.

Stadler et al., "High-Speed Couplings and Cleavages in Microwave-Heated, Solid-Phase Reactions at High Temperatures," Eur. J. Org. Chem. 2001. pp. 919-925.

Yu et al., "Enhanced Coupling Efficiency in Solid-Phase Peptide Synthesis by Microwave Irradiation," The Journal of Organic Chemistry, Aug. 28, 1992, pp. 4781-4785, vol. 57, No. 18, American Chemical Society 1992.

Erdelyi et al., "Rapid Microwave-Assisted Solid Phase Peptide Synthesis," Synthesis 2002, Aug. 22, 2002, pp. 1592-1596, No. 11.

Chen et al., "The Studies of Microwave Effects on the Chemical Reactions," Journal of the Chinese Chemical Society, 1997, pp. 169-182, vol. 44, No. 3.

Chen et al., "Enhancement of Chemical Reactions by Microwave Irradiation," Journal of the Chinese Chemical Society, 1991, pp. 85-91, vol. 38. No. 1; Only 1 page Abstract enclosed.

Olivos et al., Microwave-Assisted Solid-Phase Synthesis of Peptoids, Organic Letters, 2002, pp. 4057-4059, vol. 4, No. 23, 2002 American Chemical Society.

Rao et al., Microwave Assisted High Yielding Preparation of N-Protected 2-Deoxyribonucleosides Useful for Oligonucleotide Synthesis, Necleosides, Nucleosites & Nucleic Acids, 2002, pp. 393-400, vol. 21 (4&5), Marcel Dekker, Inc., New York.

Coleman, et al., Microwave Parallel Library Generation: Comparison of a Conventional-and Microwave-Generated Substituted 4(5)-Sulfanyl-1H-imidazole Library, J. Comb. Chem. 2002, pp. 87-93, vol. 4, American Chemical Society.

Fluorous Technology in Discovery Applications, Fluorous Technologies, Inc., 2002-2003, http://fluorous.com/scavenging.html, 3 pages.

Carpino, Principal Research Interests, Department of Chemistry—Faculty Research Areas—Louis Carpino, University of Massachusetts, http://www.chem.umass.edu/Carpino/carpino.html, 2 pages. accessed online May 9, 2003.

Chemical Synthesis of Peptides, KVL, http://kemi.kvl.dk/~prh/html/research.htm, 9 pages, accessed online May 9, 2003.

http://web.archive.org/web/20020514031700/www.sigma-genosys.com/peptide_faq.asp accessed online Nov. 9, 2007.

Answers.com: vessel. http://www.answers.com/vessel accessed online Mar. 13, 2007, 2 pages.

Gausephol et al., "Automated Synthesis of Solid-Phase Bound Peptides in Peptide Arrays on Membrane Supports: Synthesis and Applications," Joachim Koch, Michael Maler (Eds.), Springer 2002, pp. 55-68.

Cammish et al., "Instrumentation for Automated Solid Phase Peptide Synthesis, Fmoc Solid Phase Peptide Synthesis," University Press: Oxford, UK, 2000, pp. 277-302.

Schnorrenberg et al., Fully Automatic Simultaneous Multiple Peptide Synthesis in Micromolar Scale—Rapid Synthesis of Series of Peptides for Screening in Biological Assays, Tetrahedron, 1989, vol. 45, No. 24, pp. 7759-7764.

European Search Report of foreign counterpart Application No. EP 07 11 7617 mailed Feb. 16, 2010.

* cited by examiner

MICROWAVE-ASSISTED PEPTIDE SYNTHESIS

RELATED APPLICATIONS

This is a continuation of Ser. No. 12/143,979 filed Jun. 23, 2008 and now U.S. Pat. No. 7,582,728. Ser. No. 12/143,979 is a continuation of Ser. No. 10/604,022 filed Jun. 23, 2003 and now U.S. Pat. No. 7,393,920.

This application is related to Ser. No. 11/235,027; Ser. No. 11/235,328 (now U.S. Pat. No. 7,550,560), Ser. No. 11/235,329 (now U.S. Pat. No. 7,563,865), Ser. No. 11/552,153 and Ser. No. 12/433,145.

SEQUENCE LISTING

This application incorporates by reference the sequence listing submitted concurrently herewith on paper. This paper copy of the sequence listing is entitled "Sequence Listing."

BACKGROUND OF THE INVENTION

The present invention relates to solid-phase peptide synthesis (SPPS), and in particular relates to microwave-assisted techniques for SPPS.

The early part of the twentieth century saw the birth of a novel concept in scientific research in that synthetically produced peptides could greatly facilitate the study of the relationship between chemical structure and biological activity. Until that time, the study of structure-activity relationships between peptides and their biological function had been carried out using purified, naturally occurring peptides. Such early, solution-based techniques for peptide purification were plagued with problems, however, such as low product yield, contamination with impurities, their labor-intensive nature and the unpredictable solubility characteristics of some peptides. During the first half of the twentieth century some solution-based synthesis techniques were able to produce certain "difficult" peptides, but only by pushing known techniques to their limits. The increasing demand for higher peptide yield and purity resulted in a breakthrough technique first presented in 1963 for synthesizing peptides directly from amino acids, now referred to as solid-phase peptide synthesis (SPPS).

The drawbacks inherent in solution-based peptide synthesis have resulted in the near-exclusive use of SPPS for peptide synthesis. Solid phase coupling offers a greater ease of reagent separation, eliminates the loss of product due to conventional chemistries (evaporation, recrystallization, etc.), and allows for the forced completion of the reactions by adding excess reagents.

Peptides are defined as small proteins of two or more amino acids linked by the carboxyl group of one to the amino group of another. Accordingly, at its basic level, peptide synthesis of whatever type comprises the repeated steps of adding amino acid molecules to one another or to an existing peptide chain of acids.

The synthetic production of peptides is an immeasurably valuable tool in the field of scientific research for many reasons. For example, some antiviral vaccines that exist for influenza and the human immunodeficiency virus (HIV) are peptide-based. Likewise, some work has been done with antibacterial peptide-based vaccines (diphtheria and cholera toxins). Synthetically altered peptides can be labeled with tracers, such as radioactive isotopes, and used to elucidate the quantity, location, and mechanism of action of the native peptide's biological acceptor (known as a receptor). This information can then be used to design better drugs that act through that receptor. Peptides can also be used for antigenic purposes, such as peptide-based antibodies to identify the protein of a newly discovered gene. Finally, some peptides may be causative agents of disease. For example, an error in the biological processing of the beta-amyloid protein leads to the "tangling" of neuron fibers in the brain, forming neuritic plaques. The presence of these plaques is a pathologic hallmark of Alzheimer's Disease. Synthetic production of the precursor, or parent molecule, of beta-amyloid facilitates the study of Alzheimer's Disease.

These are, of course, only a few of the wide variety of topics and investigative bases that make peptide synthesis a fundamental scientific tool.

The basic principle for SPPS is the stepwise addition of amino acids to a growing polypeptide chain that is anchored via a linker molecule to a solid phase particle which allows for cleavage and purification once the coupling phase is complete. Briefly, a solid phase resin support and a starting amino acid are attached to one another via a linker molecule. Such resin-linker-acid matrices are commercially available (e.g., Calbiochem, a brand of EMD Biosciences, an affiliate of Merck KGaA of Darmstadt, Germany; or ORPEGEN Pharma of Heidelberg, Germany, for example). The starting amino acid is protected by a chemical group at its amino terminus, and may also have a chemical side-chain protecting group. The protecting groups prevent undesired or deleterious reactions from taking place at the alpha-amino group during the formation of a new peptide bond between the unprotected carboxyl group of the free amino acid and the deprotected alpha-amino of the growing peptide chain. A series of chemical steps subsequently deprotect the amino acid and prepare the next amino acid in the chain for coupling to the last. Stated differently, "protecting" an acid prevents undesired side or competing reactions, and "deprotecting" an acid makes its functional group(s) available for the desired reaction.

When the desired sequence of amino acids is achieved, the peptide is cleaved from the solid phase support at the linker molecule. This technique consists of many repetitive steps making automation attractive whenever possible.

Many choices exist for the various steps of SPPS, beginning with the type of reaction. SPPS may be carried out using a continuous flow method or a batch flow method. Continuous flow is useful because it permits real-time monitoring of reaction progress via a spectrophotometer. However, continuous flow has two distinct disadvantages in that the reagents in contact with the peptide on the resin are diluted, and scale is more limited due to physical size constraints of the solid phase resin. Batch flow occurs in a filter reaction vessel and is useful because reactants are accessible and can be added manually or automatically.

Other choices exist for chemically protecting the alpha-amino terminus. A first is known as "Boc" (Nα-t-butoxycarbonyl). Although reagents for the Boc method are relatively inexpensive, they are highly corrosive and require expensive equipment. The preferred alternative is the "Fmoc" (9-fluorenylmethyloxycarbonyl) protection scheme, which uses less corrosive, although more expensive, reagents.

For SPPS, solid support phases are usually polystyrene suspensions; more recently polymer supports such as polyamide have also been used. Preparation of the solid phase support includes "solvating" it in an appropriate solvent (dimethyl formamide, or DMF, for example). The solid phase support tends to swell considerably in volume during salvation, which increases the surface area available to carry out peptide synthesis. As mentioned previously, a linker molecule connects the amino acid chain to the solid phase resin. Linker molecules are designed such that eventual cleavage provides either a free acid or amide at the carboxyl terminus. Linkers are not resin-specific, and include peptide acids such as 4-hydroxymethylphenoxyacetyl-4'-methylbenzyhydrylamine (HMP), or peptide amides such as benzhydrylamine derivatives.

Following the preparation of the solid phase support with an appropriate solvent, the next step is to deprotect the amino acid to be attached to the peptide chain. Deprotection is carried out with a mild base treatment (picrodine or piperidine, for example) for temporary protective groups, while permanent side-chain protecting groups are removed by moderate acidolysis (trifluoroacetic acid, or TFA, as an example).

Following deprotection, the amino acid chain extension, or coupling, is characterized by the formation of peptide bonds. This process requires activation of the C-alpha-carboxyl group, which may be accomplished using one of five different techniques. These are, in no particular order, in situ reagents, preformed symmetrical anhydrides, active esters, acid halides, and urethane-protected N-carboxyanhydrides. The in situ method allows concurrent activation and coupling; the most popular type of coupling reagent is a carbodiimide derivative, such as N,N'-dicyclohexylcarbodiimide or N,N-diisopropylcarbodiimide.

After the desired sequence has been synthesized, the peptide is cleaved from the resin. This process depends on the sensitivity of the amino acid composition of the peptide and the side-chain protector groups. Generally, however, cleavage is carried out in an environment containing a plurality of scavenging agents to quench the reactive carbonium ions that originate from the protective groups and linkers. One common cleaving agent is TFA.

In short summary SPPS requires the repetitive steps of deprotecting, activating, and coupling to add each acid, followed by the final step of cleavage to separate the completed peptide from the original solid support.

Two distinct disadvantages exist with respect to current SPPS technology. The first is the length of time necessary to synthesize a given peptide. Deprotection steps can take 30 minutes or more. Coupling each amino acid to the chain as described above requires about 45 minutes, the activation steps for each acid requires 15-20 minutes, and cleavage steps require two to four hours. Thus, synthesis of a mere twelve amino acid peptide may take up to 14 hours. To address this, alternative methods of peptide synthesis and coupling have been attempted using microwave technology. Microwave heating can be advantageous in a large variety of chemical reactions, including organic synthesis because microwaves tend to interact immediately and directly with compositions or solvents. Early workers reported simple coupling steps (but not full peptide synthesis) in a kitchen-type microwave oven. Such results are not easily reproducible, however, because of the limitations of a domestic microwave oven as a radiation source, a lack of power control, and reproducibility problems from oven to oven. Others have reported enhanced coupling rates using microwaves, but have concurrently generated high temperatures that tend to cause the solid phase support and the reaction mixtures to degenerate. Sample transfer between steps has also presented a disadvantage.

Another problem with the current technology is aggregation of the peptide sequence. Aggregation refers to the tendency of a growing peptide to fold back onto itself and form a loop, attaching via hydrogen bonding. This creates obvious problems with further chain extension. Theoretically, higher temperatures can reduce hydrogen bonding and thus reduce the fold-back problem, but such high temperatures can create their own disadvantages because they can negatively affect heat-sensitive peptide coupling reagents. For this reason, SPPS reactions are generally carried out at room temperature, leading to their characteristic extended reaction times.

SUMMARY OF THE INVENTION

In one aspect, the invention is a process for the solid phase synthesis of peptides, which comprises the steps of: (a) deprotecting a first amino acid linked to a solid phase resin by removing protective first chemical groups; (b) activating chemical groups on a second amino acid to prepare the second amino acid for coupling with the first amino acid; (c) coupling the activated second amino acid to the deprotected first amino acid to form a peptide from the first and second amino acids; and (e) applying microwave energy to accelerate the deprotecting, activating, and coupling cycle.

In another aspect the invention is an apparatus for the accelerated synthesis of peptides by the solid phase method, that comprises a reaction cell that is transparent to microwave radiation; a passageway for adding liquids to the reaction cell; a passageway for removing liquids but not solids from the reaction cell; a microwave cavity for holding the cell; and a microwave source in wave communication with the cavity.

In yet another aspect, the invention is a vessel system for the accelerated synthesis of peptides by the solid phase method, the vessel system comprising: a reaction cell that is transparent to microwave radiation; a first passageway in fluid communication with the cell for transferring solid phase resin between a resin source external to the cell and the cell; a second passageway in fluid communication between at least one amino acid source and the cell for adding amino acids to the cell; a third passageway in gaseous communication with an inert gas source and with a vent for applying gas pressure to and releasing gas pressure from the cell so that the controlled flow of gases to and from the cell can be used to add and remove fluids and flowing solids to and from the cell.

In yet another aspect the invention is a process for accelerating the solid phase synthesis of peptides, and comprising: deprotecting a protected first amino acid linked to a solid phase resin by admixing the protected linked acid with a deprotecting solution in a microwave transparent vessel while irradiating the admixed acid and solution with microwaves; activating a second amino acid by adding the second acid and an activating solution to the same vessel while irradiating the vessel with microwaves; coupling the second amino acid to the first acid while irradiating the composition in the same vessel with microwaves; and cleaving the linked peptide from the solid phase resin by admixing the linked peptide with a cleaving composition in the same vessel while irradiating the composition with microwaves.

DETAILED DESCRIPTION

The invention is an apparatus and method for the solid phase synthesis of one or more peptides, specifically utilizing microwave energy to accelerate the method.

Figure 1:
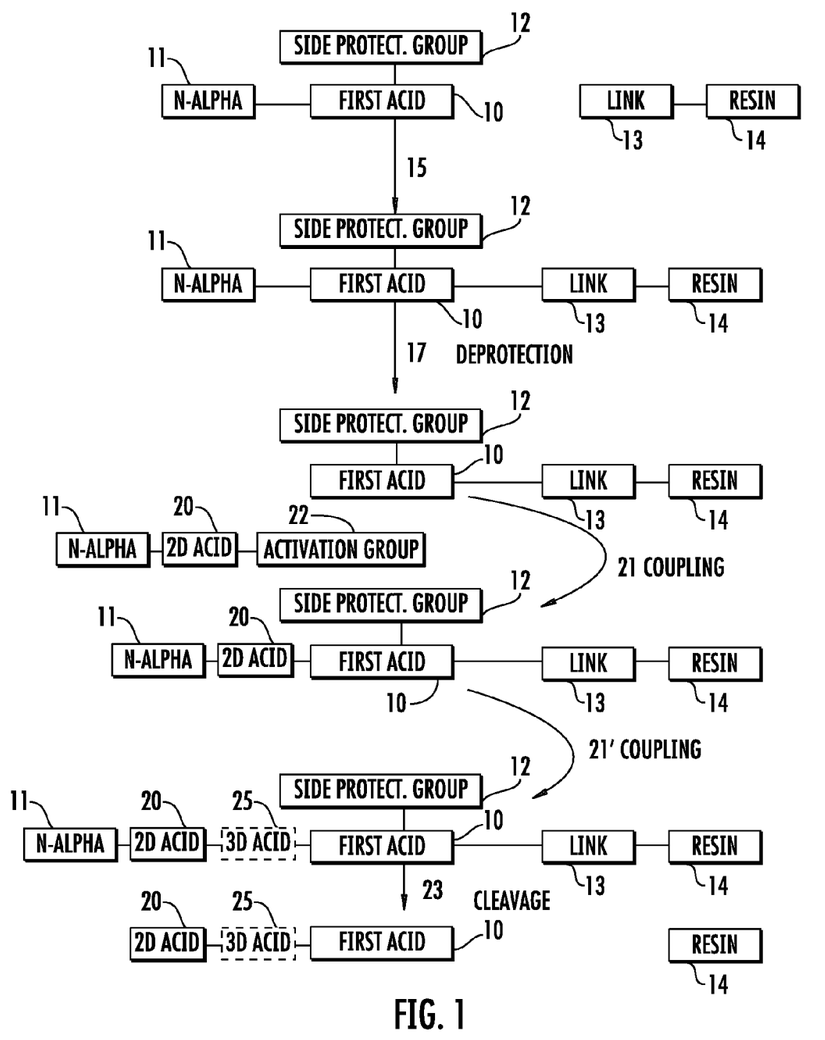
FIG. 1 is a schematic diagram illustrating certain aspects of solid phase peptide synthesis.

FIG. 1 is a schematic diagram illustrating some aspects of the solid phase peptide synthesis process. It will be understood that FIG. 1 is general in nature and is not limiting of the invention. FIG. 1 illustrates a first amino acid 10 that includes an N-alpha protective group 11 and a side chain protective group 12 attached to it. A linking molecule 13 is attached to a resin support 14. In a first step designated by the arrow 15, the first acid and its protective groups 11 and 12 are attached to the linker 13 and the resin support 14. In a second step indicated by the arrow 17, the N-alpha protective group is removed ("deprotected") to produce the structure in which the first acid 10 and its side chain-protecting group 12 are linked to the support 14 through the linker molecule 13. In the next step, indicated by the arrow 21, the first amino acid 10 is coupled to a second amino acid designated at 20, which similarly has an N-alpha protective group 11 and an activation group 22 attached to it to encourage the coupling. Following the coupling step 21, the resulting structure includes the first acid 10 and the second acid 20 connected to one another and still including the N-alpha protective group 11 attached to the second acid 20 and the side chain protective group 12 attached to the first acid 10 with the connected acids being in turn linked to the support 14 through the linking molecule 13. Additional acids, represented by the broken rectangle 25 are added in the same manner (arrow 21') to lengthen the peptide chain as desired.

In the final step, the connected acids 10, 20 and 25 are cleaved, represented by the arrow 23, from the protective groups and the support to result in the desired peptide separate from the resin support 14. The coupling steps can, as indicated a number of times elsewhere herein, be repeated as many times as desired to produce a resulting peptide.

Figure 2:
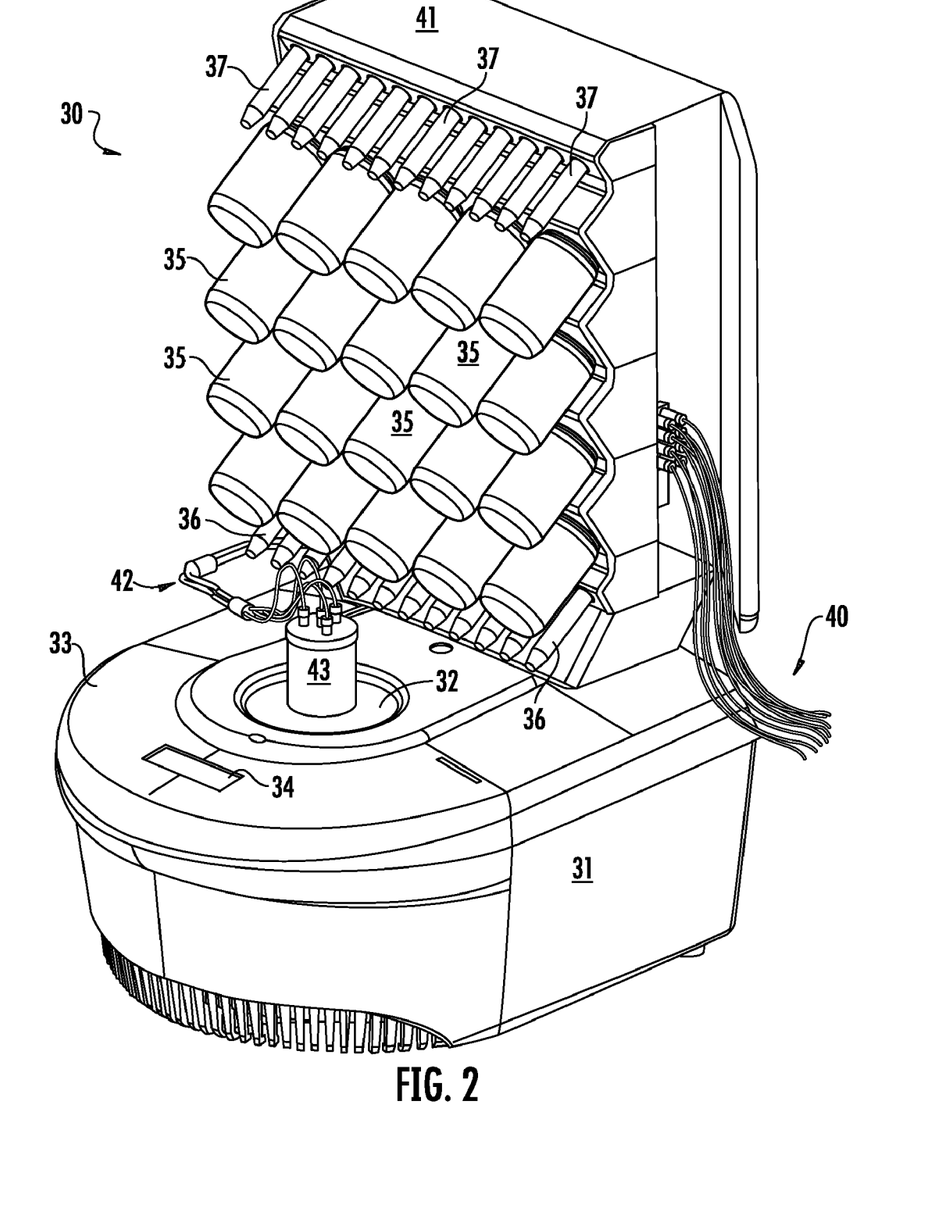
FIG. 2 is a perspective view of a synthesis instrument according to the present invention.

FIG. 2 illustrates one commercial embodiment of the present invention broadly designated at 30. FIG. 2 illustrates some of the broad structural aspects of the invention, the details of which will be explained with respect to FIGS. 3 and 6.

First, FIG. 2 illustrates the microwave portion of the device 31. The portion of the instrument that applies microwave irradiation to the vessel is preferably a single-mode cavity instrument that can be controlled to apply suitable amounts of power to the sample sizes and materials used in the method of the invention. In the preferred embodiment of the invention, the microwave portion of the instrument has the design and operation that is set forth in a number of co-pending and commonly assigned U.S. patents and applications. These include U.S. published applications Nos. 20030089706, 20020117498, 20030199099 and 20040020923; and U.S. Pat. No. 6,744,024. The disclosures of all of these references are incorporated entirely herein by reference. Commercial versions of such single-mode microwave instruments are available from the assignee of the present invention, CEM Corporation, of Matthews, N.C., under the DISCOVERY™, VOYAGER™, and EXPLORER™ trade names.

With those considerations in mind, FIG. 2 illustrates the location of the cavity 32, the housing 33, and an appropriate display 34, for providing instructions or information during operation. A plurality of amino acid source containers or bottles are each respectively indicated at 35. The respective resin containers are illustrated at 36, and the product peptide containers are designated at 37. A series of fluid passageways are illustrated by the portions of tubing broadly designated at 40 and will be discussed in more detail with respect to FIG. 6. Similarly, the instrument 30 includes an upper housing portion 41, which includes an appropriate manifold, for physically transporting the fluids and resins in the manner described herein. Although the manifold is not illustrated, it can comprise any series of passageways and valves that serve to direct the fluids in the manner described herein and particularly described with respect to the circuit diagram of FIG. 6.

Thus, in the embodiment illustrated in FIG. 2, up to 20 different amino acids can be incorporated in the respective containers 35, and up to 12 different peptides can be produced and placed in the respective containers 37 in automated fashion. It will be understood that these are commercial embodiment numbers, however, and that the invention is neither limited to this number nor does it need to have as many sources or product containers as are illustrated.

Figure 3:
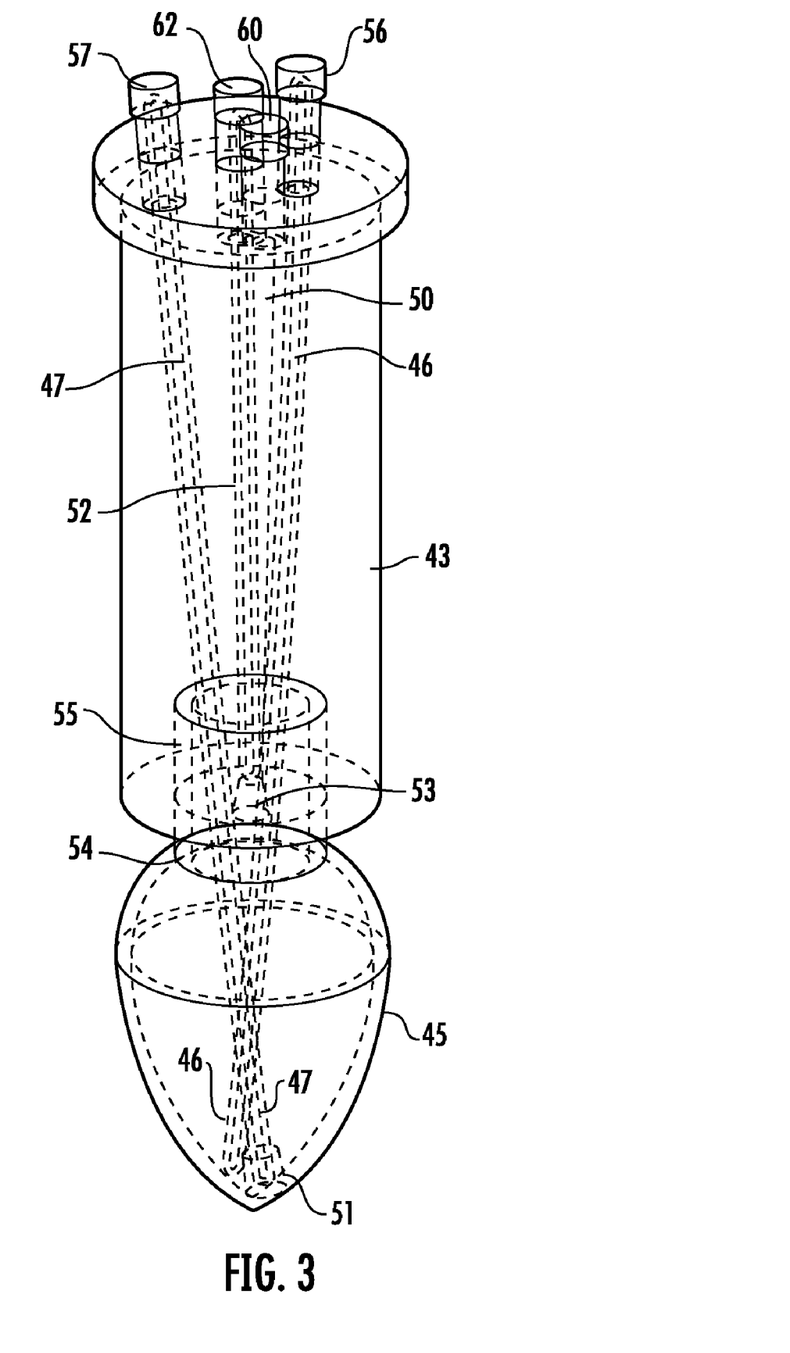
FIGS. 3, 4 and 5 are perspective views of a reaction vessel and adapter according to the present invention.
Figure 4:
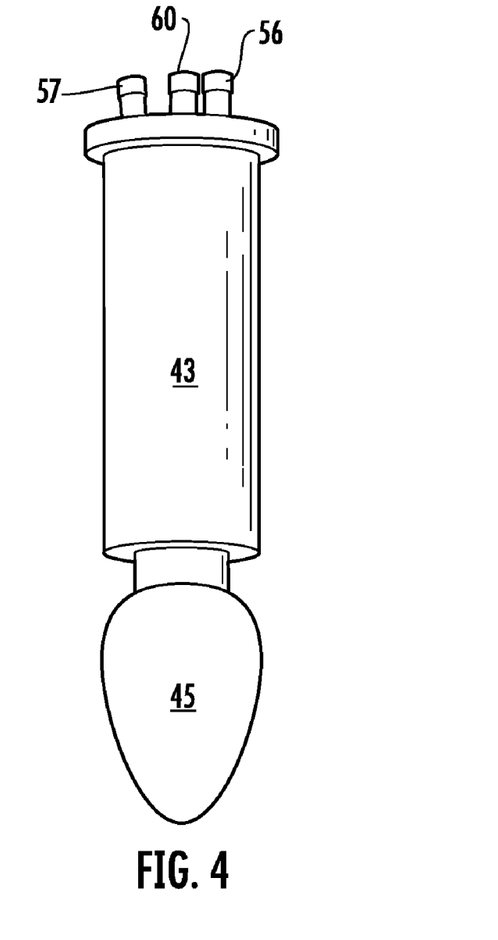
Figure 5:
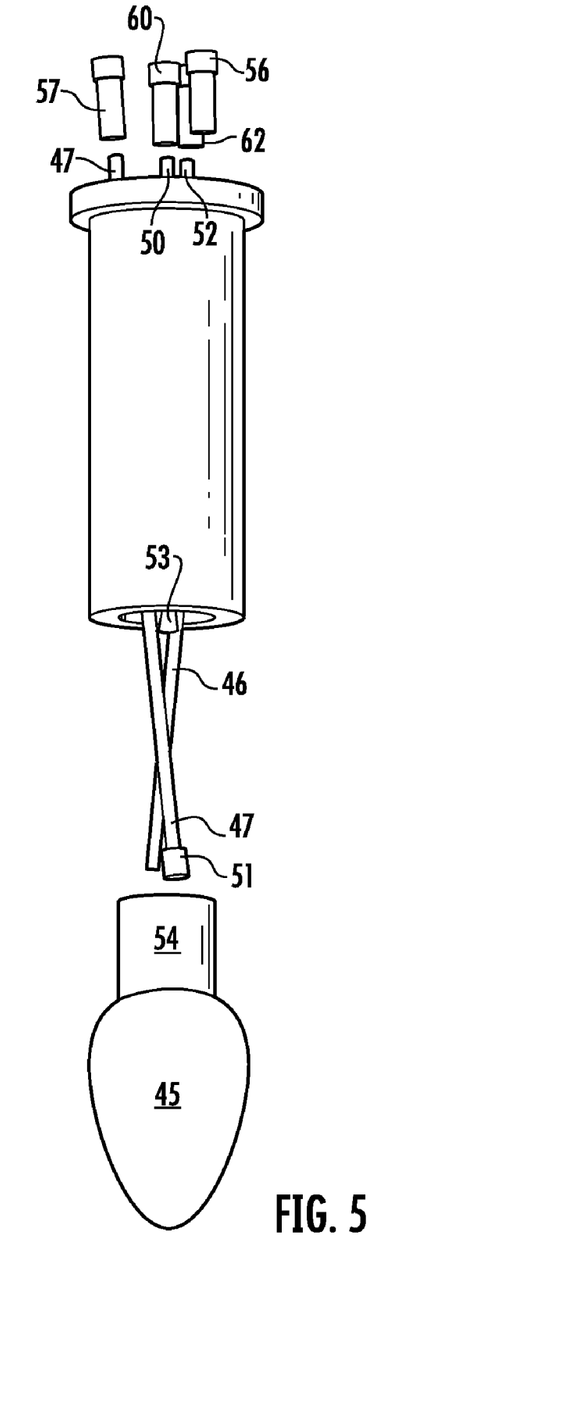

FIG. 2 also illustrates a complimentary series of passageways shown as the tubing broadly designated at 42 that are immediately connected to the reaction vessel adapter 43, which is partially illustrated in FIG. 2, but is described in more detail with respect to FIGS. 3, 4, and 5.

FIG. 3 is a partial perspective view of the reaction vessel 45 and the vessel adapter 43, portions of which were also illustrated in FIG. 2. The reaction vessel 45 is preferably pear-shaped and formed of a material that is transparent to microwave radiation. Preferred materials include, but are not limited to, glass, Teflon, and polypropylene. A first passageway, shown as the tubing 46, is in fluid communication with the reaction vessel (or "cell," the terms are used interchangeable herein) 45 for transferring solid phase resin between a resin source external to the cell 45 and the cell 45. A second passageway 47 is in fluid communication between at least one amino acid source (FIG. 6) and the cell 45 for adding amino acids to the cell 45. A third passageway 50 is in gas communication with an inert gas source (FIG. 6) and with a vent (FIG. 6) for applying and releasing gas pressure to and from the cell 45, so that the controlled flow of gas in the manifold and to and from the cell 45 can be used to add and remove fluids and flowing solids to and from the cell 45.

FIG. 3 also illustrates that the second passageway 47 also includes a filter, shown as the frit 51, for preventing solid-phase resin from entering the second passageway 47 from the cell 45.

In preferred embodiments, the invention further comprises a fourth passageway 52, in fluid communication between an external solvent source (FIG. 6) and the cell 45 for flushing the cell 45 with solvent. As illustrated in FIG. 3, the fourth passageway 52 includes a spray head 53 or equivalent structure for adding the solvent to the cell 45.

The adapter 43 is formed of a microwave transparent and chemically inert material, which is preferably formed of a polymer, such as a fluorinated polymer (e.g., PTFE) or an appropriate grade of polypropylene. The adapter 43 is preferably a solid cylinder with the passageways 46, 47, 50, and 52 drilled or bored therethrough. The passageways 46, 47, 50, 52 can simply comprise the bore holes through the adapter 43, but preferably may also include tubing, which again is formed of a microwave transparent, chemically inert material such as PTFE, PTFE variations, or polypropylene. The tubing is preferably ⅛ inch outside diameter and 1/16 inch inside diameter.

Although not illustrated in FIG. 3 (to reduce the complexity of the drawing), the vessel neck 54 preferably is externally threaded and engages an internally threaded bore hole 55 in lower portions of the adapter 43. The threaded engagement between the vessel 45 and the adapter 43 permits secure engagement between these two items, and also permits the vessel 45 to be easily engaged and disengaged to and from the adapter 43. In particular, differently sized vessels or vessels formed of different materials can be substituted and still fit the adapter 43, provided the necks are of the same size and threading.

As some final details, FIG. 3 also includes threaded fittings 56, 57, 60, and 62 to the respective first, second, third and fourth passageways 46, 47, 50 and 52. These permit the entire adapter 43 and vessel 45 to be easily connected to and removed from the remainder of the instrument 30.

FIGS. 4 and 5 are respective assembled and exploded perspective drawings of the adapter of FIG. 3, and thus illustrate the same elements. Both figures include the adapter 43 and the cell 45. The threaded fittings 57, 60, 56, and 62 are visible in FIG. 5, with 57, 60 and 56 also visible in 54. The exploded view of FIG. 5 also illustrates portions of the first and second passageways, 46, 47, as well as the threaded vessel neck 54 and the board opening 55 in the lower portions of the adapter 43.

Figure 6:
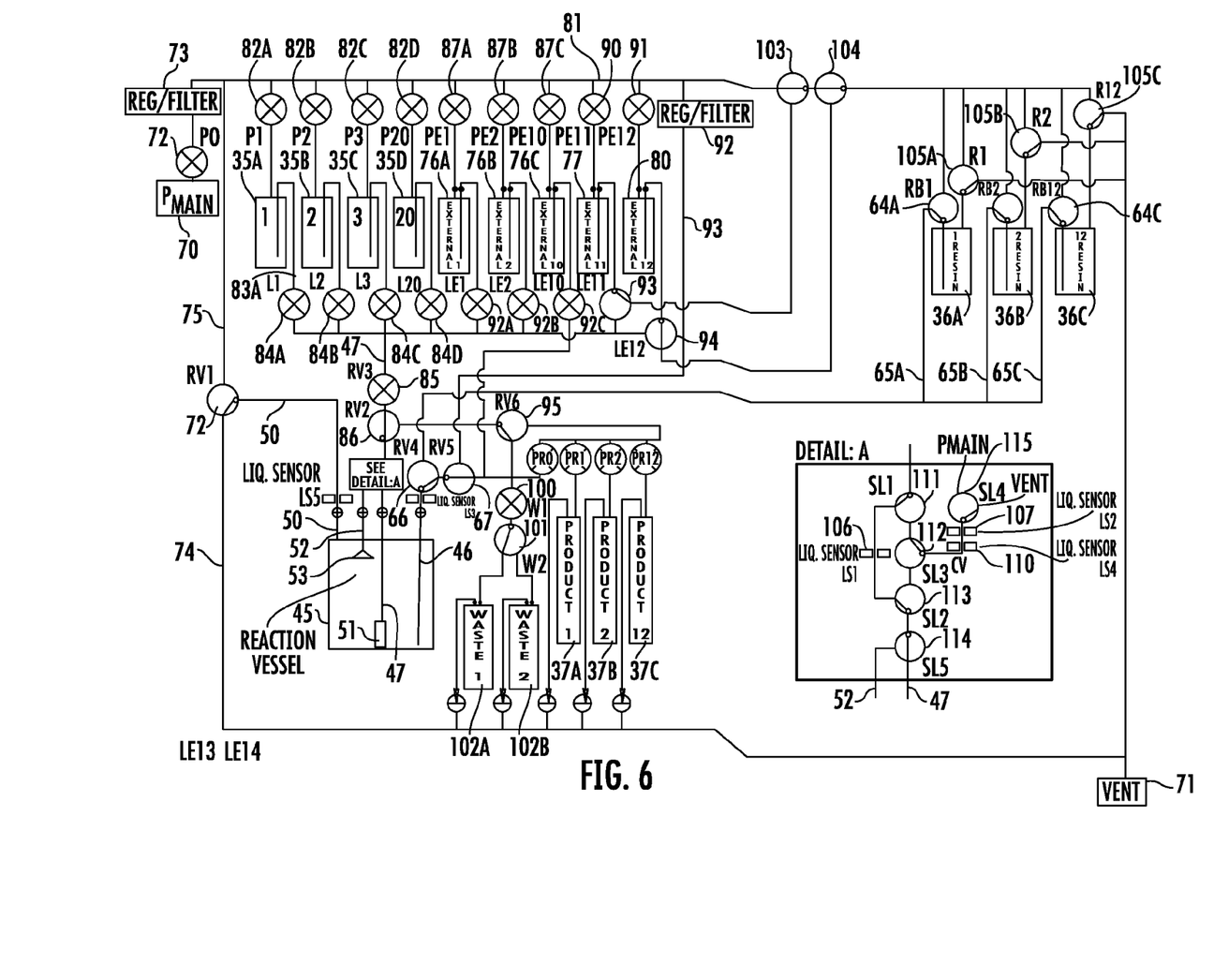
FIG. 6 is a flow circuit diagram illustrating aspects of the present invention.

FIG. 6 is a flow circuit diagram for the present invention. Wherever possible, the elements illustrated in FIG. 6 will carry the same reference numerals as in the other drawings. Because most of the elements symbolized in FIG. 6 are commonly available and well understood, they will not be described in particular detail, as those of skill in this art can practice the invention based on FIG. 6 without undue experimentation.

Accordingly, FIG. 6 illustrates a vessel system for the accelerated synthesis of peptides by the solid-phase method. The vessel system comprises the reaction cell (or vessel) 45, which is indicated in FIG. 6 schematically as a square. Otherwise, the reaction cell 45 has all of the characteristics already described and which will not be repeated with respect to FIG. 6. The first passageway 46 is in fluid communication with the cell 45 for transferring solid phase resin between an external resin source 36 and the cell 45. Three resin sources, 36 (A, B and C) are illustrated in FIG. 6 and correspond to the resin sources 36 illustrated in FIG. 2. As set forth with respect to FIG. 2, the number of resin sources is elective rather than mandatory with 12 being shown in the embodiment of FIG. 2, and three illustrated in FIG. 6 for purposes of simplicity and schematic understanding. Each of the resin sources 36 is in communication with a respective three-way valve 64, A, B and C, and, in turn, to an appropriate resin line 65, A, B and C and then another three-way valve 66 adjacent to cell 45 for delivering resin through the first passageway 46 into the cell 45. The three-way valve 66 is immediately in communication with another three-way valve 67, the purpose of which will be described shortly.

FIG. 6 also shows the second passageway 47, which is in communication with at least one of the amino acid sources 35, which are illustrated again as rectangles in the upper portions of FIG. 6. The schematically illustrated amino acid sources or containers 35 correspond to the containers 35 illustrated in FIG. 2.

The third passageway 50 is in gas communication with an inert gas source 70 and with a vent 71 for applying gas pressure to and releasing gas pressure from the cell 45, so that the controlled flow of gasses to and from the cell 45 can be used to add and remove fluids and flowing solids to and from the cell. The third passageway 50 accomplishes this in conjunction with at least one valve 72 which, depending upon its orientation, permits the third passageway 50 to communicate with either the gas source 70 or the vent 71. The gas source can be any gas that can appropriately be pressurized and that does not otherwise interfere with the chemistry of the peptide synthesis or the elements of the instrument itself. Thus, a number of inert gases are suitable, with pressurized nitrogen being typically favored for reasons of wide availability, lower cost, ease of use, and lack of toxicity. FIG. 6 illustrates that the nitrogen supply 70 is controlled through a two-way valve 72 and an appropriate regulator 73, which also may include a filter. In the orientation of FIG. 6, the gas line from the two-way valve 72 to the vent 71 is labeled at 74, and the passageway from the valve 72 to the regulator 73 is designated at 75.

FIG. 6 also illustrates the filter 51 in the second passageway 47 for preventing the solid phase resin from entering the second passageway from the cell 45.

FIG. 6 also illustrates the fourth passageway 52 along with the spray head 53. As described with respect to FIG. 3, the fourth passageway 52 is in fluid communication with one or more external solvent sources three of which are illustrated at 76, A, B and C. Two other external solvent sources 77 and 80 are separately labeled because of their optionally different fluid paths.

FIG. 6 also illustrates the manner in which the pressurized gas from the source 70 can be used to both deliver compositions to, and then remove them from, the reaction cell 45 as desired whether they be peptides, solvent, wastes, or resin. Thus, in one aspect of such delivery, FIG. 6 illustrates a gas passage 81 that communicates with several items. First, the gas passageway 81 communicates with a series of two-way valves designated at 82A, B, C and D that each provide a gas passage when the respective valve is open to its corresponding amino acid container 35. Pressurized gas entering a container 35 pushes the acid through the respective delivery lines 83A, B, C or D, which in turn communicates with a respective acid valves 84 A, B, C and D and then with the second passageway 47 and its respective two-way valve 85 and three-way valve 86. To illustrate, when valves 82A and 84A are open, and the remaining valves 82B, C and D are closed, gas from the source 70 can be directed through the gas passage 81, through valve 82A, into amino acid bottle 35A, from the bottle 35A through the valves 84A, 85 and 86, and then into the cell 45.

The respective valves are automated in order to provide the cell with the desired composition (e.g. resin, solvent, acid) at the appropriate point in the synthesis, as well as to remove compositions from the cell (peptides, waste) at other appropriate points. The required programming and processor capacity is well within the capability of a personal computer-type processor (e.g. PENTIUM III®), and the use of automated controls and sequences is generally well understood in this and related arts, e.g. Dorf, The Electrical Engineering Handbook, 2d Ed. (CRC Press 1997).

It should be understood that while many amino acids exist, the twenty source containers of this apparatus are intended, but not limited to, contain the twenty "common" amino acids for synthesizing proteins that are well known to those skilled in this art. These commercially available common amino acids can be purchased in chemically "protected" form (also from Sigma-Aldrich) to prevent unwanted and/or deleterious reactions from occurring.

Solvent can be delivered to the cell in an analogous manner. The solvents communicate with the gas passage 81 through the valves 87A, B and C and 90 and 91. This places the gas in direct communication with the external solvent tanks 76A, B and C and 77 and 80. External solvent tanks 76A, B and C are further in communication with respective two-way valves 92A, B and C and respective three-way valves 93 and 94.

These all lead, when the valves are appropriately oriented, to the second passageway 47 for delivering solvent to the reaction vessel 45 using gas pressure in the same manner that the acids are delivered. A TFA solvent is used in external reservoirs 76C and thus can be directed through alternative lines for optional isolation.

FIG. 6 also indicates that the gas source 70 can be used to drive items from the cell 45 directly by closing all of the valves to the amino acids and the external solvent reservoirs, and then directing the gas through the regulator and filter 92 and its associated passageway 93 directly to valves 67 and 66 and then into the first passageway 46 and the cell 45.

Alternatively, the first passageway 46 can be used to empty the cell 45. In this aspect, valve 72 is set to direct gas from the source 70 and through the passage 75 to the valve 72 and through the third passageway 50 and into the cell. The gas pressure then directs fluids in the cell 45 through either second passageway 47 or first passageway 46 depending upon the orientation of the valves 86, 66 and 67. FIG. 6 also illustrates an additional three-way valve 95 that can direct product to the product containers 37A, B and C, which correspond to the product containers 37 illustrated in FIG. 2. An appropriate set of product valves 96A, B and C can be opened or closed as desired to direct the desired peptide product to the desired product container 37A, B or C.

Alternatively, depending upon the orientation of valves 86, 66, 67 and 95, and together with additional two-way valve 100 and three-way valve 101 adjacent to waste containers 102A and 102B, materials can be directed from the cell 45 to either of the waste containers 102A and B.

The pressurized gas from the source 70 can also be used to deliver resin. In this aspect, the pressurized gas is directed through the gas passage 81 and through the three-way valves 103 and 104. With respect to delivery of resin, however, when both of the valves 103 and 104 are open to the resin containers, they direct the pressurized gas to three respective valves 105A, B and C which in turn are in communication with the resin containers 36 and the exit valves 64A, 64B and 64C which then use the gas pressure delivered to force the resin through the resin line 65 and eventually to the first passage 46 for delivery into the reaction vessel 45.

The resin sources may contain variable amounts and kinds of resins, including, but not limited to, Wang resins, Trityl resins, and Rink acid labile resins; the resins are commercially available from vendors such as Sigma-Aldrich Corp., Saint Louis, Mo. 63101.

Solvent can be directed to the resin containers 36A, B, C, from the external reservoirs 77, 80 using the valves 103, 104 between the solvent reservoirs and the resin containers.

FIG. 6A is a more detailed illustration of the valving system adjacent the reaction vessel 45. In particular, FIG. 6A shows a series of liquid sensors 106, 107 and 110 in conjunction with a series of three-way valves 111, 112, 113, 114 and 115. The operation of the valves in accordance with the sensors permits a metered amount of liquid to be added to the reaction vessel 45 as may be desired or necessary. For example, with the valves 111, 113 and 114 shown in the orientation of FIG. 6A, fluid can flow directly from valve 86 all the way to those portions of second passageway 47 that extend immediately into the reaction vessel 45. Alternatively, if valve 111 is open towards valve 112, liquid will flow through valves 111 and 112 until it reaches the liquid sensors 107 and 110. The liquid sensors inform the system when a proper or desired amount of liquid is included, which can then be delivered by changing the operation of valve 112 to deliver to the valve 113, and then to the valve 114, and then to the second passageway 47 and finally into the cell 45 as desired.

Thus, in overall fashion, FIG. 6 illustrates the delivery of precursor compositions (amino acids, solvents, resin, deprotectants, activators) from their respective sources to the single reaction cell and the further delivery of products and by-products (peptides, waste, cleaved resin) from the cell to their respective destinations. It will be understood that the particular flow paths and valve locations illustrate, rather than limit, the present invention.

Figure 7:
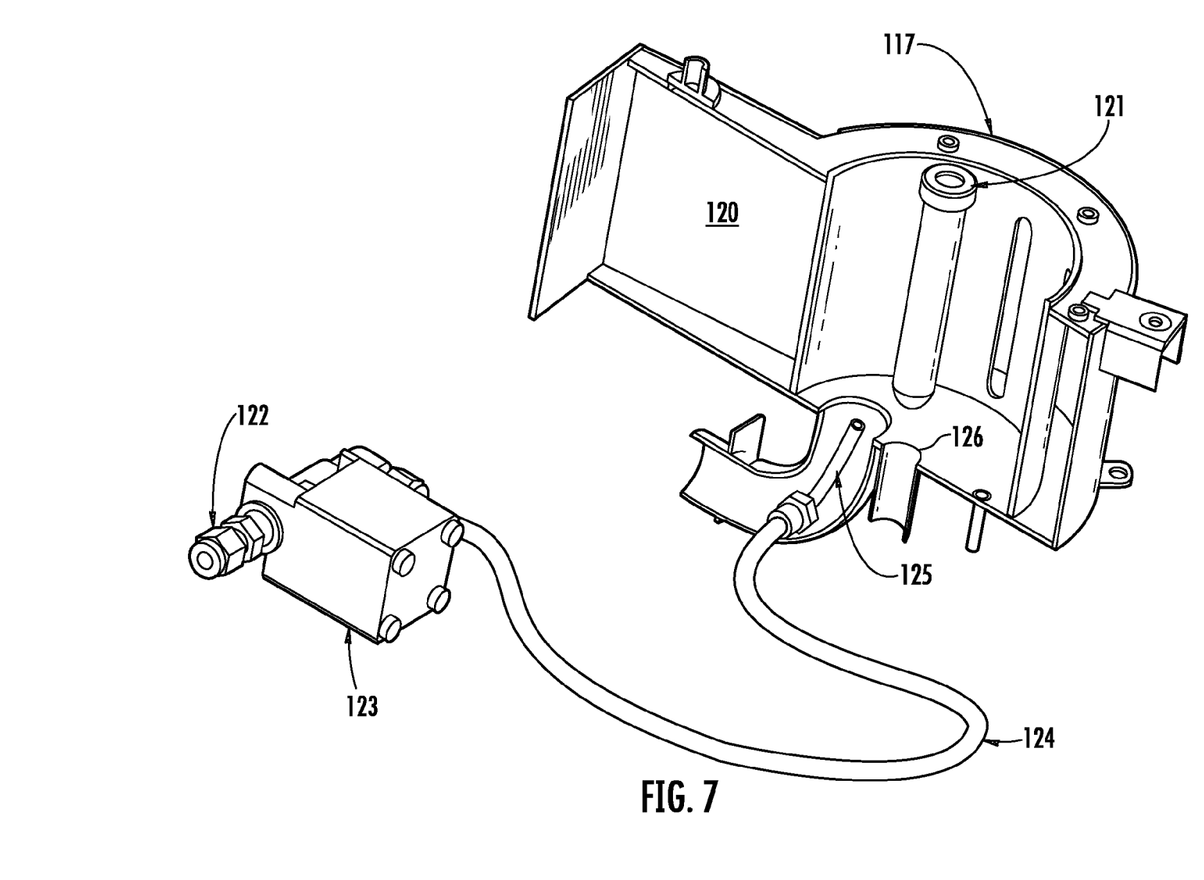
FIG. 7 is a cut-away perspective view of the cavity and waveguide of the present invention.

As noted earlier, the microwave instrument portions of the synthesis instrument can essentially be the same as those set forth in a number of commonly assigned and co-pending U.S. patent applications. Accordingly, FIG. 7 is included to highlight certain aspects of the microwave portion of the instrument without overly burdening the specification herein. In particular, FIG. 7 is essentially the same as FIG. 1 in previously incorporated application Ser. No. 10/064,261 filed Jun. 26, 2002. FIG. 7 illustrates a microwave cavity 117 shown in cutaway fashion for clarity. The cavity is attached to a wave guide 120, which is in microwave communication with an appropriate source (not shown). Microwave sources are widely available and well understood by those of ordinary skill in this art, and include magnetrons, klystrons, and solid state diodes. FIG. 7 illustrates a test tube-shaped cell 121 in the cavity 117 and such can be used if desired for the reactions of the present invention, although the pear-shaped vessel 45 is generally preferred.

In order to carry out the simultaneous cooling, the instrument includes a cooling gas source (not shown) which delivers the cooling gas to the inlet fitting 122 on the flow valve 123 (typically a solenoid). During active cooling, the solenoid 123, which is typically software controlled, directs cooling gas through the tubing 124 and to the cooling nozzle 125, which directs the cooling gas on to the reaction vessel 121.

It should be pointed out, however, that other cooling mechanisms may be adapted to this method, such as a stream of refrigerated air or a liquid cooling mechanism that circulates refrigerated liquid around the reaction cell in a manner that would not interfere with the transfer of microwave energy.

FIG. 7 also illustrates a cylindrical opening 126, which is typically used to permit temperature observation of the reaction vial 121. Such temperature observation can be carried out with any appropriate device, which can normally include a fiber optic device of the type that can measure the temperature of an object by reading the infrared radiation produced by the object. Such devices are well understood in the art, and will not be discussed in further detail herein, some aspects having already been discussed in the incorporated references.

In preferred embodiments, the microwave source is capable of, but not limited to, "spiking" microwave energy. In other words, the microwave source is capable of generating high power for a short length of time as opposed, but not limited to, low power for a longer period of time. This feature aids in preventing the undesirable effect of overheating the contents of the reaction vessel and appears to increase the rate of reaction as well.

The apparatus optionally includes an infrared photosensor for measuring temperature. The infrared sensor does not contact the reaction cell contents, yet still accurately measures the average temperature of the reaction cell contents and not merely the air temperature surrounding the contents. Infrared temperature analysis is more accurate, non-intrusive, and allows for a more simplified apparatus design compared to a probe or the like, which measures only a localized area and would require physical contact of the contents.

The second passageway is further characterized by a filter which prevents the passage of resin. Additionally, the first and second passageways are in fluid communication with each other with respect to the movement of liquid solvents and flowing solids; herein the term "flowing solids" refers to resin, with or without amino acids or peptides attached, and suspended in an appropriate solvent.

In another aspect, the invention is a method for the solid phase synthesis of one or more peptides that incorporates the use of microwave energy. Microwave energy applied to the contents of the reaction cell during the deprotecting, activating, coupling, and cleaving steps greatly decreases the length of time necessary to complete these reactions. The method for applying microwave energy may be moderated by the microwave source in such a way as to provide the fastest reaction time while accumulating the least amount of heat, thus more microwave energy may be applied and heat-associated degradation of the reaction cell contents does not occur. This method includes, but is not limited to, spiking the microwave energy in large amounts for short lengths of time.

The method optionally includes the synthesis of a complete peptide of two or more amino acids in a single reaction vessel, and may include the coupling of one or more amino acids to one or more amino acids that are attached to the solid phase resin.

The method includes cooling the reaction cell, and thus its contents, during and between applications of microwave energy up to and including the final cleaving step. The cooling mechanism of the method operates during amino acid extension cycles, the term "cycle" used herein to refer to the deprotection, activation, and coupling necessary to link one amino acid to another. The cooling system can also operate during and between applications of microwave energy in a given cycle to keep the bulk temperature of the reaction cell contents down. The cooling system can also operate when the complete peptide is cleaved from the resin.

Alternatively, it has also been discovered that controlling the power, rather than strictly controlling the temperature, can also provide a desired control over the progress of a reaction. As noted elsewhere herein, the use of a variable or switching power supply can help serve this purpose, an example of which is given in commonly assigned U.S. Pat. No. 6,288,379; the contents of which are incorporated entirely herein by reference.

The method includes agitating the contents of the reaction cell with nitrogen gas in order to promote maximal exposure of the resin and any attached amino acids or peptides to solvents and free amino acids.

In a preferred embodiment, the method comprises transferring a first common amino acid linked to a resin of choice, both suspended in an appropriate solvent, to the reaction cell via pressurized nitrogen gas. A deprotection solution is then pumped into the reaction cell. This process is accelerated by the application of microwave energy, and the heat generated by the microwave energy is minimized by a cooling mechanism. Multiple deprotection steps may be executed. The deprotection solution is then withdrawn from the reaction cell, leaving the deprotected, common amino acid linked to the resin. After several (three to five) resin washes of approximately one resin volume each using an appropriate solvent and removing the wash solvent, the next "free" common amino acid or acids (dissolved in solution) is added to the reaction cell along with an activating solution. The activation of the free amino acid is accelerated by the application of microwave energy, and the reaction cell temperature is controlled by a cooling mechanism as described above. The method further comprises coupling the free amino acid or acids to the deprotected, linked amino acid, forming a peptide, using microwave energy to accelerate the method. As above, heat generated by the microwave energy is minimized by a cooling mechanism. The coupling step is further preferred to include nitrogen agitation of the reaction cell contents. Completion of this step represents one cycle of one or more amino acid addition. Following the coupling step, the activation solution is withdrawn and the resin is washed as above. The cycle is repeated until the desired peptide sequence is synthesized. Upon completion of peptide synthesis, a further deprotection step may be carried out to remove protective chemical groups attached to the side chains of the amino acids. This deprotection step is carried out as described above. The resin containing the attached, completed peptide is then washed as above with a secondary solvent to prepare the peptide for cleavage from the resin. Following the removal of the secondary solvent, cleaving solution is added to the reaction cell and cleaving is accelerated by the application of microwave energy, and the heat generated by the microwave energy is minimized by a cooling mechanism. Upon completion of cleaving, the peptide product is transferred to a product tube. Optionally, the peptide may be "capped" at any point during the synthesis process. Capping is useful to terminate incompletely coupled peptides, assist in proper folding of the peptide sequence, and to provide a chemical identification tag specific to a given peptide. However, these modifications decrease the solubility of synthetic peptides and thus must be carefully considered. Capping is carried out for example, but not limited to, using acetic anhydride or fluorous capping in solid phase synthesis, or by attaching any of a large variety of chemical groups such as biotin to either the N-terminal, C-terminal or side chain of a peptide.

In another embodiment, the invention comprises de-protecting first amino acid linked to a solid phase resin by removing protective first chemical groups, activating chemical groups on a second amino acid to prepare the second amino acid for coupling with the first amino acid, coupling the activated the second amino acid to the de-protected first amino acid to form a peptide from the first and second amino acids, cleaving the peptide from the solid phase resin, applying microwave energy to accelerate the de-protected, activating and coupling cycle, and applying microwave energy to accelerate the cleaving step.

It is, of course, the usual procedure to add a number of amino acids to one another to form a peptide sequence. Accordingly, the method can, and usually, comprises repeating the de-protecting, activating and coupling cycle to add third and successive acids to form a peptide of a desired sequence.

In that regard, it will be understood that as used herein, terms such as "first," "second," or "third" are used in a relative rather than absolute sense.

In a particularly preferred embodiment, the method comprises successively de-protecting, activating and coupling a plurality of amino acids into a peptide in a single vessel without removing the peptide from the solid phase resin between the cycles. This, and additional aspects, of the invention will be understood with regard to the discussion of the figures.

In another embodiment, the method comprises proactively cooling the vessel and its contents during the application of microwave energy to thereby prevent undesired degradation of the peptide or acids by limiting heat accumulation that would otherwise result from the application of the microwave energy.

As is typical in peptide synthesis, the de-protecting step comprises de-protecting the alpha-amino group of the amino acid, but can also comprise de-protecting side chains on the amino acids of the peptide, both under the microwave and radiation. Similarly, the activating step typically comprises activating the alpha-carboxyl group of the second amino acids.

Because the amino acids and peptides are sensitive to excessive heat, and in addition to the proactive cooling step just described, the step of applying the microwave energy can comprise "spiking" the application of microwave energy to relatively short-time intervals to thereby prevent undesired degradation of the peptidal acids by limiting heat accumulation that could be encouraged by the continuous application of the microwave energy. As used herein, the term "spiking" refers to the limitation of the application of microwave energy to the relative short time intervals. Alternatively, the microwave power can be supplied from a switching power supply as set forth in commonly assigned U.S. Pat. No. 6,288,379, the contents of which are incorporated entirely herein by reference.

In other embodiments, the peptide synthesis process can comprise activating and coupling in situ using a carbodiimide type coupling free agent.

In another aspect, the invention is a process for accelerating the solid phase synthesis of peptides. In this aspect, the method comprises deprotecting a protected first amino acid linked to a solid phase resin by admixing the protective linked acid with a deprotecting solution in a microwave, transparent vessel while irradiating the admixed acid and solution with microwaves, and while cooling the admixture (or alternatively controlling the applied power, or both) to prevent heat accumulation from the microwave energy from degrading the solid phase support or any of the admixed compositions. In particular, the method comprises deprotecting the alpha-amino group of the amino acid, and most typically with a composition suitable for removing protective chemicals selected from the group consisting of fmoc and boc. As is known to those familiar with this chemistry, the deprotecting step can also comprise deprotecting the side chain of the amino acid. In those circumstances, the deprotecting step comprises using a composition suitable for removing t-butyl-based side chain protecting groups.

Following the deprotecting step, the method comprises activating a second amino acid by adding this second amino acid and an activating solution to the same vessel while irradiating the vessel with microwaves and while simultaneously cooling the vessel to prevent heat accumulation from the microwave energy from degrading the solid face support or any of the admixed compositions.

The method next comprises coupling the second amino acid to the first acid while irradiating the composition in the same vessel with microwaves, and while cooling the admixture to prevent heat accumulation from the microwave energy from degrading the solid phase support or any of the admixed compositions.

Finally, the method comprises the step of cleaving the linked peptide from the solid phase resin by admixing the linked peptide with a cleaving composition in the same vessel while irradiating the composition with microwaves, and while cooling the vessel to prevent heat accumulation from the microwave energy from degrading the solid phase support or the peptide.

The activating step can also comprise activating and coupling the second amino acid using an in situ activation method and composition such as phosphorium or uranium activators, HATU, HBTU, PyBOP, PyAOP, and HOBT.

Once again, because the synthesis of peptides almost always includes the addition of three or more acids into the chain, the method can comprise cyclically repeating the steps of deprotecting, activating and coupling for three or more amino acids in succession to thereby synthesize a desired peptide.

In a particular embodiment of the invention, the successive steps of deprotecting, activating, coupling and pleading are carried out in the single reaction vessel without removing the peptide from the solid phase resin or from the vessel between cycles.

The method can further comprise agitating the admixture, preferably with nitrogen gas during one or more of the deprotecting, activating, coupling and pleading steps. Any gas can be used for the agitation, provided it does not otherwise interfere with the synthesis chemistry, the peptides or the amino acids, but nitrogen is typically preferred for this purpose because of its wide availability, low cost and chemical inertness with respect to the particular reactions.

Experimental:
Peptide: Asn-Gly-Val
MW=288
Scale=0.10 mmol
Resin used=Fmoc-Val-Wang Resin
Resin substitution=0.27×10-3 moles/gram resin
Microwave Protocol:
For all reactions in this peptide the microwave power was initially set at 50 W then regulated to maintain the temperature below 60° C.

Deprotection: A 20% Piperidine in DMF solution was used for deprotection. The reaction was performed for 30 seconds in microwave, and then repeated with new deprotection solution for 1:00 minute in microwave.

Coupling: Activation was performed with 0.40 mmol HCTU, 0.80 mmol DIPEA, and 0.40 mmol of each Fmoc-amino acid for each coupling in the synthesis. Approximately 10 mL of DMF was used to dissolve the mixture. The reaction was performed for 5:00 min. in the microwave.

Washing: The vessel was filled with approximately 10 mL of DMF and rinsed 5 times after each deprotection and coupling step.

Cleavage: Cleavage was performed with 95% TFA and 5% $H_2O$ for 90:00 min.

Peptide was precipitated in 50 mL of cold ethyl ether overnight. Product was collected and dried. Mass Spectrum was obtained of crude product from electrospray ionization mass spectrometry using a ThermoFinnigan Advantage LC/MS.

Figure 8:
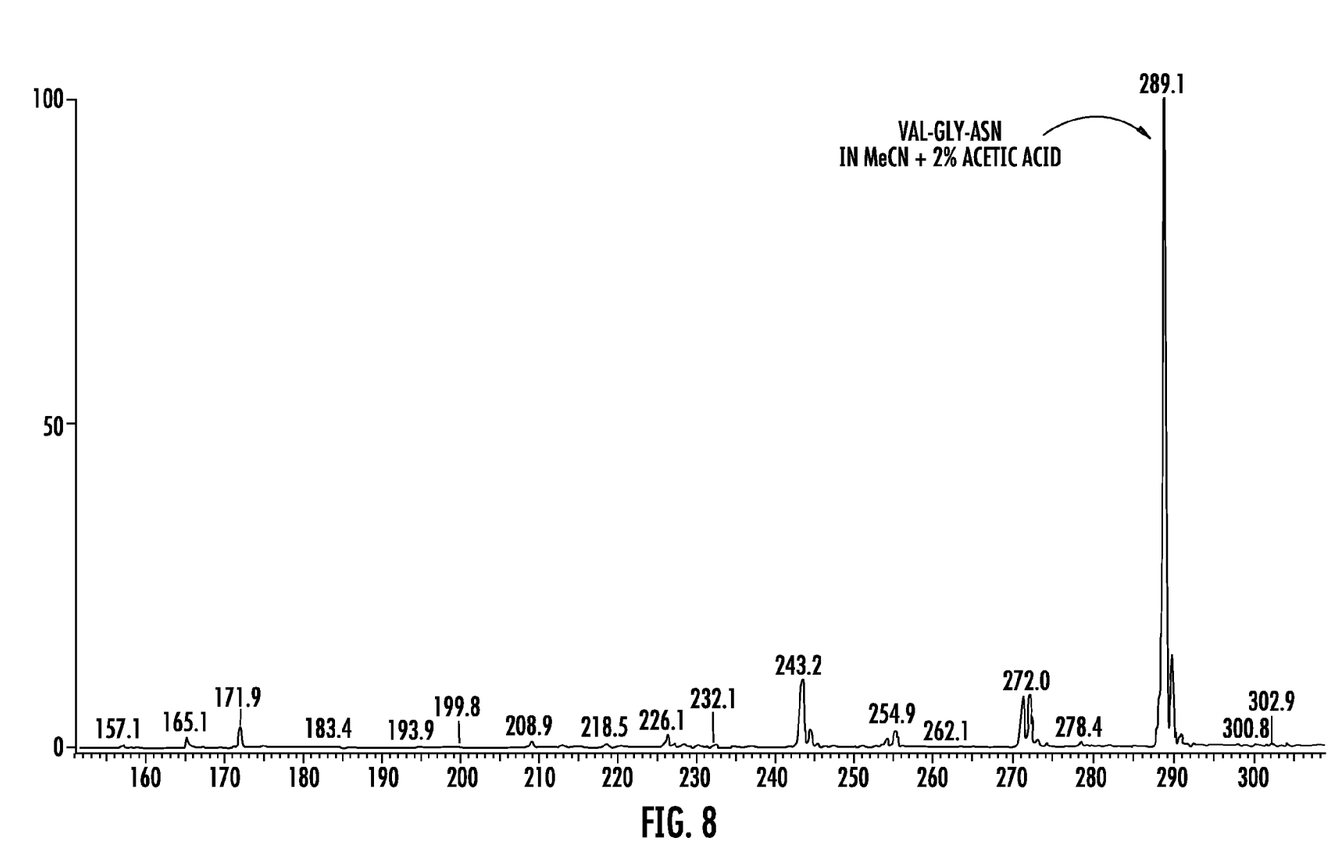
FIG. 8 is the mass spectrum of one peptide synthesized according to the method of the invention.

Results: The Electrospray Ionization Mass Spectrum (FIG. 8) showed a single peak at 289.1 corresponding to the MW of Asn-Gly-Val. No other peaks corresponding to incomplete couplings were observed.

Peptide: Gly-Asn-Ile-Tyr-Asp-Ile-Ala-Ala-Gln-Val (SEQ ID NO: 1)
MW=1062
Scale=0.25 mmol
Resin used: Fmoc-Val-Wang Resin
Resin substitution=0.27×10-3 moles/gram resin
Microwave Protocol:
This peptide was synthesized with a power time control method.

Deprotection: A 20% Piperidine in DMF solution was used for deprotection. The deprotection was performed with 25 W of microwave power for 30 seconds, and then repeated with new deprotection solution for 1:00 min. in the microwave.

Coupling: Activation was performed with 0.9/1.0 mmol of HBTU/HOBt respectively, 2 mmol of DIPEA, and 1.0 mmol of Fmoc-amino acid for each coupling in the synthesis. Approximately 15 mL of DMF was used to dissolve the mixture. The coupling reaction was done in 5:00 min. in the microwave with power alternating between on for 15 seconds and off for 45 seconds. The first cycle of power was 25 W, and the remaining four were each 20 W.

Washing: The vessel was filled with approximately 15 mL of DMF and rinsed 5 times after each deprotection and coupling step.

Cleavage: Cleavage was performed with 95% TFA, 2.5% H2O, and 2.5% TIS.

Peptide was precipitated in 100 mL of cold ethyl ether overnight. Product was collected and dried. Mass Spectrum was obtained of crude product from electrospray ionization mass spectrometry using a ThermoFinnigan Advantage LC/MS.

Figure 9:
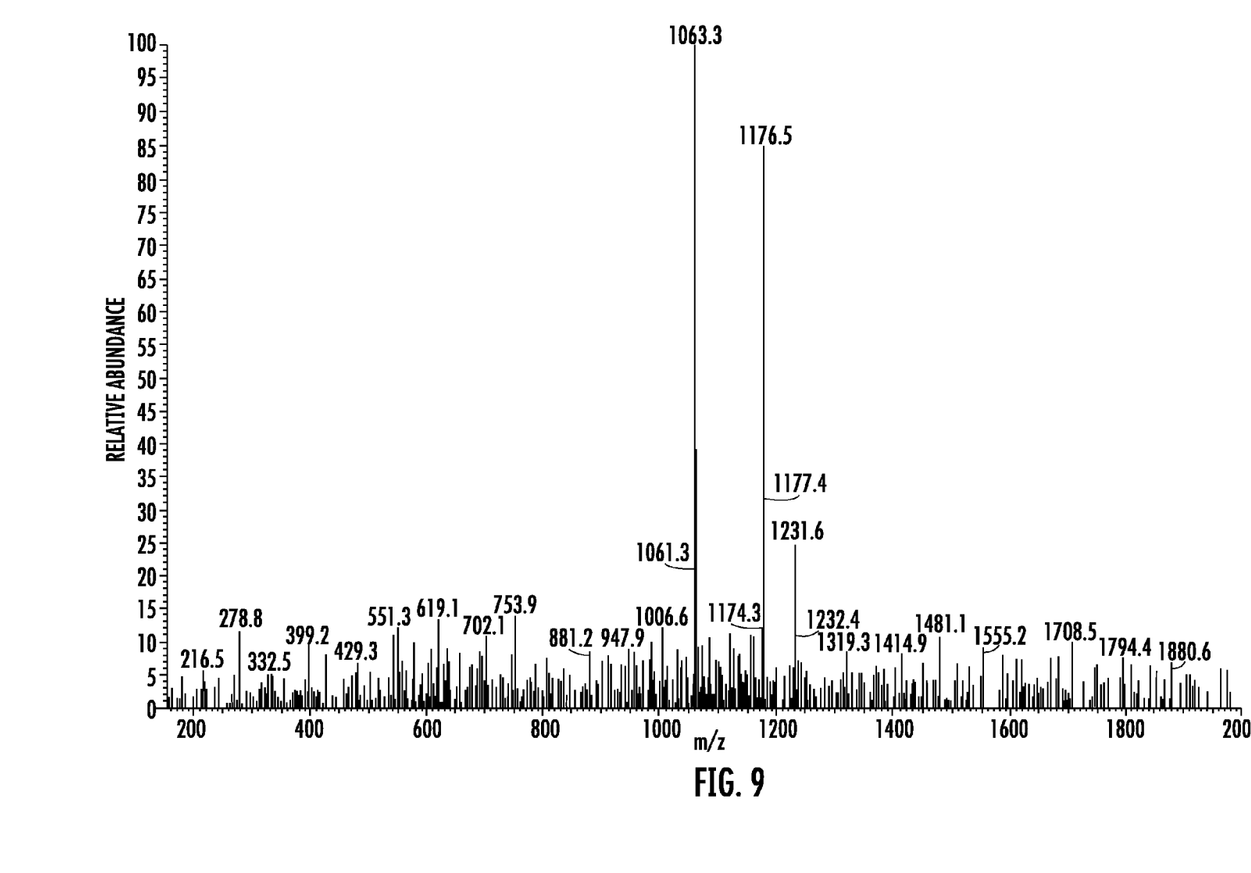
FIG. 9 is the mass spectrum of a second peptide synthesized according to the method of the invention.

Results: The Electrospray ionization mass spectrum (FIG. 9) shows a peak at 1063.3 that corresponds to the desired peptide mass. No peaks were detected for incomplete couplings. A second peak was obtained at 1176.5 that corresponds to the desired peptide with an extra Ile amino acid. This corresponds to incomplete removal of the deprotection solution before one of the Ile coupling reactions and allowing two Ile amino acids to be added to the peptide.

In the drawings and specification there have been disclosed typical embodiments of the invention. The use of specific terms is employed in a descriptive sense only, and these terms are not meant to limit the scope of the invention being set forth in the following claims.

The invention claimed is:

1. A process for the solid phase synthesis of peptides, which comprises:
   (a) transferring solid phase resin particles between a resin source external to a single microwave transparent vessel and into the microwave transparent vessel;
   (b) deprotecting a first amino acid linked to the solid phase resin particles by removing protective chemical groups from the first acid;
   (c) activating chemical groups on a second amino acid to prepare the second amino acid for coupling with the first amino acid;
   (d) coupling the activated second amino acid to the deprotected first amino acid to form a peptide from the first and second amino acids;
   (e) accelerating at least the deprotecting and coupling steps by applying microwave energy during the deprotecting, and coupling steps; and
   (f) successively deprotecting, and coupling a plurality of amino acids into a peptide in the single microwave transparent vessel without removing the peptide from the single vessel between cycles.

2. A process according to claim 1 comprising cleaving the peptide from the solid phase resin particles while applying microwave energy to accelerate the cleaving step.

3. A process according to claim 1 comprising transferring the solid phase resin particles through a passageway between the resin source and the microwave transparent vessel.

4. A process according to claim 1 comprising transferring the solid phase resin particles into the microwave transparent vessel and then solvating the resin.

5. A process according to claim 1 comprising transferring the solid phase resin particles as a flowing solid into the microwave transparent vessel.

6. A peptide synthesis process according to claim 1 comprising successively deprotecting, and coupling a plurality of amino acids into a peptide in the single vessel without removing the peptide from the solid phase resin particles between cycles.

7. A peptide synthesis process according to claim 1 comprising proactively cooling the vessel and its contents during the application of microwave energy to thereby prevent undesired degradation of the peptide or acids by limiting heat accumulation that would otherwise result from the application of the microwave energy.

8. A peptide synthesis process according to claim 1 wherein the deprotecting step comprises deprotecting the alpha-amino group of the amino acid.

9. A peptide synthesis process according to claim 1 further comprising deprotecting side chains on the amino acids of the peptide under microwave irradiation.

10. A peptide synthesis process according to claim 1 wherein the activating step comprises activating the alpha-carboxyl group of the second amino acid.

11. A peptide synthesis process according to claim 1 wherein the step of applying the microwave energy comprises limiting the application of microwave energy to relatively short time intervals to thereby prevent undesired degradation of the peptide or acids by limiting heat accumulation that could be encouraged by the continuous application of the microwave energy.

12. A peptide synthesis process according to claim 1 further comprising activating and coupling using a in situ method and a composition selected from the group consisting of phosphorium activators, uronium activators, HATU, HBTU, PyBOP, PyAOP, and HOBT.

13. A peptide syntheses process according to claim 1 comprising monitoring the temperature of the vessel and moderating the applied power based upon the monitored temperature.

14. A peptide synthesis process according to claim 1 comprising moderating the applied power based on the status of the reaction.

15. A peptide synthesis process according to claim 1 further comprising activating the second amino acid in situ.

16. A peptide synthesis process according to claim 1 further comprising activating the second amino acid using a composition selected from the group consisting of preformed symmetrical anhydrides, active esters, acid halides, and urethane-protected N-carboxyanhydrides.

17. A process for accelerating the solid phase synthesis of peptides, and comprising:
- deprotecting the alpha-amino group of a first amino acid protected with a composition selected from the group consisting of Na-9-fluorenylmethyloxycarbonyl (Fmoc) and Na-t-butoxycarbonyl (Boc) and linked to solid phase resin particles by admixing the protected linked acid with a deprotecting solution in a microwave transparent vessel while irradiating the admixed acid and solution with microwaves;
- activating a second amino acid;
- coupling the second amino acid to the first acid while irradiating the composition in the same vessel with microwaves; and
- successively deprotecting, and coupling a plurality of amino acids into a peptide in the same microwave transparent vessel without removing the peptide from the same vessel between cycles.

18. A peptide synthesis process according to claim 17 comprising cooling the vessel during any one or more of the deprotecting and coupling steps to prevent heat accumulation from the microwave energy from degrading the solid phase support or the peptide.

19. A peptide synthesis process according to claim 17 comprising cyclically repeating the steps of deprotecting and coupling for three or more amino acids in succession to thereby synthesize a desired peptide.

20. A peptide synthesis process according to claim 17 comprising cleaving the peptide from the solid phase resin particles.

21. A peptide synthesis process according to claim 17 further comprising agitating the admixture with nitrogen gas during one or more of the deprotecting, activating, coupling, and cleaving steps.

22. A peptide synthesis process according to claim 17 comprising deprotecting the side chain of the amino acid.

23. A peptide synthesis process according to claim 22 comprising deprotecting the side chain of the amino acid with a composition suitable for removing t-butyl-based side chain protecting groups.

24. A peptide synthesis process according to claim 17 further comprising activating and coupling the second amino acid in situ using a carbodiimide-type coupling reagent.

25. A peptide synthesis process according to claim 17 further comprising activating the second amino acid using a composition selected from the group consisting of preformed symmetrical anhydrides, active esters, acid halides, and urethane-protected N-carboxyanhydrides.

26. A peptide synthesis process according to claim 17 comprising cleaving the linked peptide from the solid phase resin by admixing the linked peptide with a cleaving composition in the same vessel while irradiating the composition with microwaves.

27. A peptide synthesis process according to claim 26 further comprising using a cleaving composition of trifluoroacetic acid and containing a plurality of scavenging agents to quench the reactive carbonium ions that originate from the protective groups and linkers.

* * * * *

UNITED STATES PATENT AND TRADEMARK OFFICE
CERTIFICATE OF CORRECTION

PATENT NO. : 8,058,393 B2  
APPLICATION NO. : 12/549445  
DATED : November 15, 2011  
INVENTOR(S) : Jonathan McKinnon Collins et al.

Page 1 of 1

It is certified that error appears in the above-identified patent and that said Letters Patent is hereby corrected as shown below:

In the Specification

In the DESCRIPTION, Column 2, Lines 64-65:

delete: "support tends to swell considerably in volume during salvation, which increases the surface area available to carry out"

and insert: -- support tends to swell considerably in volume during solvation, which increases the surface area available to carry out --

Signed and Sealed this  
Twenty-sixth Day of November, 2013

Margaret A. Focarino  
*Commissioner for Patents of the United States Patent and Trademark Office*

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Microwave-Assisted Peptide Synthesis

<400> SEQUENCE: 1

Gly Asn Ile Tyr Asp Ile Ala Ala Gln Val
1               5                   10
```